United States Patent [19]

Dickakian

[11] Patent Number: 4,671,103
[45] Date of Patent: Jun. 9, 1987

[54] METHOD FOR DETERMINING CRUDE OIL FOULING BY HIGH PERFORMANCE LIQUID CHROMATOGRAPHY

[75] Inventor: Ghazi B. Dickakian, Kingwood, Tex.

[73] Assignee: Exxon Chemical Patents Inc., Linden, N.J.

[21] Appl. No.: 720,840

[22] Filed: Apr. 8, 1985

[51] Int. Cl.$^4$ ............................................. G01N 30/00
[52] U.S. Cl. .................................. 73/61.1 C; 73/61.2; 210/656
[58] Field of Search ........................... 73/61.1 C, 61.2; 422/70; 436/161; 210/656, 638, 662, 672

[56] References Cited

U.S. PATENT DOCUMENTS 4,341,634  7/1982  Matsushita et al. ............ 436/161 X Primary Examiner—Stewart J. Levy
Assistant Examiner—Joseph W. Roskos
Attorney, Agent, or Firm—R. L. Graham

[57] ABSTRACT

The invention features the fractionating of crude oils into component parts of saturate, neutral aromatic, and polar aromatic fractions, using high performance liquid chromatography techniques. Analysis of the various fractions can be used to predict the tendency of the crude oil to cause fouling of refinery heatexchanger equipment.

5 Claims, No Drawings

METHOD FOR DETERMINING CRUDE OIL FOULING BY HIGH PERFORMANCE LIQUID CHROMATOGRAPHY

FIELD OF INVENTION:

The present invention relates to a test method for determining the tendency of crude oil to foul heat-exchanger equipment in oil refineries and more particularly to a test method for determining which fractions of the crud oil have the tendency to form deposits that clog heat-exchanger conduits and reduce their heat transfer capabilities.

BACKGROUND OF THE INVENTION

Different crude oils have different precipitating and fouling characteristics with regard to heated oil refinery surfaces. The problem of predicting the offending substances in a particular crude oil which foul heat-exchanger equipment in oil refineries and petrochemical plants has been virtually unresolved. Fouling of hydrocarbon streams, consisting of carbonaceous deposits on heat exchanger surfaces, leads to a blockage of flow and a decrease in heat transfer. Both resulting conditions severly reduce efficiency in the processing of the crude oil. If it can be predicted which fractions of the crude oils are troublesome, measures can be taken in advance to prevent this fouling by either removing the offending substances causing the deleterious deposits, or by adding antifouling additives to the flow stream to reduce deposit formation. Therefore, it would be most desirable to be able to predict these fouling substances.

There are a number of methods available for determining the rates of fouling of hydrocarbon streams. Conceptually, they are all similar in that they attempt to measure the change in heat transferred from a heated surface to a test fluid.

One approach is to use a test unit which is configured to allow measurement of the fluid temperature at the exit of the heat-exchanger while the metal temperature of the heated tube is controlled. This configuration provides for close simulation of refinery and petrochemical plant heat-exchanger operations and provides for measurement of the significant effect of fouling which is indicated by the reduction of heat transfer. The test unit provides for a thermal fouling evaluation of the crude oil in an accelerated test which is designed to reproduce the fouling problem experienced in a refinery over several months. Acceleration is provided by carrying out test operating temperatures higher than those in a particular refinery unit, so that the prospective level of fouling can be produced in a reasonable period of time (usually 3-4 hours). Heat transfer data is obtained by holding the heater tube at a constant temperature, while measuring the change in the liquid outlet temperture. As fouling progresses, i.e., a carbonaceous deposit build up on the heater tube surface, a decrease in the fluid outlet temperture results when using a constant outlet liquid temperature operation. The change in liquid outlet temperature with time provides the basic heat data required for comparative evaluation of untreated material and additive-treated material. The rate of change in outlet liquid temperature versus time shows relative fouling tendencies.

Present test equipment is only capable of measuring the overall tendency of crude oils to foul refinery apparatus, and cannot predict which are the offending susbstances or fractions.

It is an object of this invention to provide an improved test which will predict the fouling tendency of crude oils. These and other objects of the invention will be apparent from the following text.

SUMMARY OF INVENTION

The present invention has developed a test procedure for determining the concentrations of the components of the crude oil that result in the fouling of the surfaces exposed to the heated crude oils.

Crude oils, being a hydrocarbon fluid can be fractionated into three separate and specific components: a hydrocarbon saturate fracton; a neutral hydrocarbon aromatic fraction; and a third fraction comprising aromatic components containing sulfur, oxygen and nitrogen (polar aromatic fraction).

The present invention utilizes high performance liquid chromatography to separate and quantify the aforementioned fractions in crude oils that are characterized by a tendency to foul refinery equipment. When these fractions are compared with the fractions similarly obtained from non-fouling crude oils, the substances causing fouling were identified.

The fouling characteristics of crude oils or other hydrocarbon fluids is measured by determining quantitively the composition of the hydrocarbon fluid by High Performance Liquid Chromatography (hereinafter referred to as HPLC) using highly specific column and procedure. The hydrocarbon fluid is separated quantitively into three previously identified specific fractions; a hydrocarbon saturate fraction, a neutral hydrocarbon aromatic fraction and a third fraction comprising the aromatics fraction containing sulfur, oxygen and nitrogen (polar aromatic fraction). The amount of neutral aromatics and polar aromatics present in the hydrocarbon fluid gives valuable information to predict the fouling tendency of the fluid to be tested. In fouling crude oils, the saturate fractions are generally in excess of 75% by weight of the total crude oil. Similarly, the aromatic fractions tend to be less than 25% by weight of fouling crude oils.

The above fractions are separated on a chromatographic column using high performance liquid chromatography techniques. The respective saturate, neutral aromatic and polar aromatic fractions are then quantitatively measured. This data is then utilized to determine whether the crude oil has a tendency to cause fouling.

Thus, the foregoing objectives have been met by a test method for determining the tendency of a crude oil, including fractions thereof, to foul refinery equipment comprising the steps of separting said crude oil into a saturated fraction and an aromatic fraction and measuring at least one of the respective weights of said saturated fraction and said aromatic fraction whereby the tendency of said crude oil to foul said equipment is determined.

DETAILED DESCRIPTION OF THE INVENTION

Crude oils like other heavy hydrocarbons, are composed of two major parts; high molecular weight asphaltene (fraction insolubles in paraffinic solvents) and a lower molecular weight asphaltene-free oil. The asphaltene and the oil fraction vary significantly in their chemical structure, coking characteristics, thermal characteristics, average molecular weight and distribution. The following Table 1 illustrates the varying differences in the characteristics of a typical heavy hydrocarbon, its asphaltene and oil fractions:

TABLE I

|  | Total Hydrocarbon | Oil | Asphaltene |
|---|---|---|---|
| Aromatic Rings | 3 to 7+ | 3,4,5 | 7+ |
| Average mol. wt. | 250 | 190 | 800 |
| Coking yield | 8 | 3 | 65 |
| Aromatic carbon (atom %) | 65 | 60 | 69 |
| Carbon Hydrogen atomic ratio | 0.97 | 0.90 | 1.19 |
| Melting point (°C.) | liquid | liquid | 190 |

Asphaltenes present in heavy hydrocarbons have high molecular weight and very broad molecular weight distribution, sometimes with molecular weights up to 10,000.

Generally speaking, the invention uses High Performance Liquid Chromatography (HPLC) to separate and measure various fractions of crude oils. HPLC is fully described in a book by L. R. Snyder et al entitled "Introduction to Modern Liquid Chromatography".

HPLC separates successfully (95%+recovery) crude oils into the three fractions that are the key in determining the crude composition. These fractions are: a saturate fraction, neutral aromatic fraction, and a polar aromatic fraction. The repeatability of the HPLC composition analysis is very good. Duplicate tests made on two crudes showed very good agreement.

HPLC systems are available in hundreds of different configurations from the basic, low cost single pump system to fully automated multi-solvent gradient systems.

The separations by HPLC are accomplished by pumping solvent/sample through a column which is packed with materials optimized for efficient separations. Separation results from differences in the extent to which the various components in the mixture interact with the column packing material. If there is little or no interaction, the component(s) will be retained in the column packing resulting in increasing elution time. Each component elutes from the column at a slightly different time, where it is detected and collected.

A basic HPLC unit is composed of a mobile phase reservoir, a pump for solvent delivery, a sample injector, a chromatography column, a detector, a recorder and data handling equipment. High-efficiency HPLC separation is achieved by using a combination of correct column, good LC apparatus, good operation and specialized know-how.

Typical chemical structures of neutral hydrocarbon aromatics oxygen and sulfur containing aromatics as determined by high resolution mass spectroscopy are presented below:

TABLE II

TYPICAL NEUTRAL AROMATICS IN CRUDE OIL

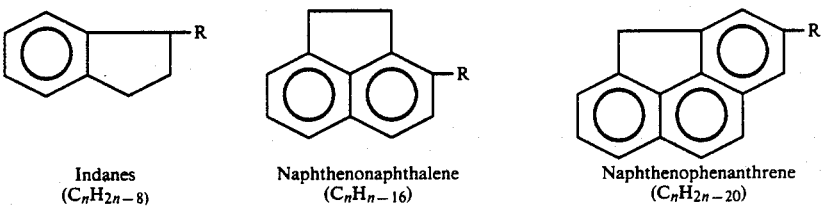

Indanes ($C_nH_{2n-8}$)   Naphthenonaphthalene ($C_nH_{n-16}$)   Naphthenophenanthrene ($C_nH_{2n-20}$)

TYPICAL SULFUR CONTAINING AROMATICS IN CRUDE OIL

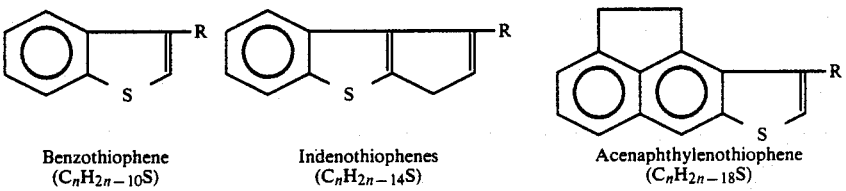

Benzothiophene ($C_nH_{2n-10}S$)   Indenothiophenes ($C_nH_{2n-14}S$)   Acenaphthylenothiophene ($C_nH_{2n-18}S$)

TYPICAL OXYGEN-CONTAINING AROMATICS IN CRUDE OIL

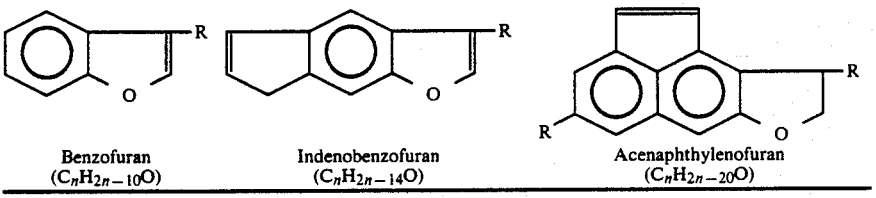

Benzofuran ($C_nH_{2n-10}O$)   Indenobenzofuran ($C_nH_{2n-14}O$)   Acenaphthylenofuran ($C_nH_{2n-20}O$)

Fouling is believed to be caused by the incompatibility of the high molecular weight asphaltenes and saturates (insolubles in paraffinic solvents) and the lower molecular weight fractions of the crude oil.

Using a test unit as earlier described, it has been found that the fouling characteristics of a high-fouling crude oil can be reduced by removing the asphaltene from the crude oil (as by deasphaltenation by liquid extraction with n-heptane). Further, it has also been demonstrated that the addition of asphaltenes (increased from 3.0% to 9.0%) to a crude oil increase dramatically its fouling tendencies.

Asphaltene-oil incompatibility appears to be a major factor in defining the fouling characteristics of a crude oil. Furthermore, the composition of the crude oil fraction without asphaltene is a major factor in determining asphaltene - oil compatibility, especially the presence of neutral and polar aromatics in the oil. Aromatics with a solubility parameter of around 12 are excellent solvents and/or dispersants for the high molecular weight asphaltenes.

High-fouling crude oils were found to contain a high saturate fraction (more than 75%) and lower neutral aromatics, polar aromatics or total aromatic fractions (less than 25%).

HPLC compositions of four different crude oils were investigated, and showed that two high-fouling crude oils contained a high saturates fraction, according to Table III, below.

TABLE III

| Crude Oil | Saturate Fraction (%) | Fouling ΔT (°F.) |
| --- | --- | --- |
| Baytown/2 | 87.90 | 55 (High Fouling) |
| Baytown/1 | 86.30 | 58 (High Fouling) |
| Coastal | 74.5 | 25 (Moderate Fouling) |
| SJV | 55.0 | 0 (Low Fouling) |

Composition of the low-fouling crude oils investigated, showed that they contained high neutral aromatic, polar aromatic or total aromatic fractions, according to Table IV, below:

TABLE IV

| Oil Sample | Neutral Aromatic Fraction % | Polar Aromatic Fraction % | Total Aromatic Fraction % | Fouling ΔT (°F.) |
| --- | --- | --- | --- | --- |
| SJV | 21.1 | 21.8 | 42.9 | 0 (Low Fouling) |
| Coastal | 16.7 | 8.8 | 25.5 | 25 (Moderate Fouling) |
| Baytown/2 | 6.9 | 2.3 | 9.2 | 55 (High Fouling) |
| Baytown/1 | 10.9 | 2.9 | 13.8 | 58 (High Fouling) |

All of the Examples cited herein demonstrating the fouling characteristics of crude oils utilized as a laboratory test apparatus known as the Thermal Fouling Tester.

The tester is a modification of the Alcor Jet Fuel Oxidation Testor described in ASTM Vol. 50 D-3241. It is configured to allow measurement of the fluid temperature at the exit of the heat-exchanger while the metal temperature of the heated tube is controlled. The test thus measures the change in temperature of a fluid which has been pumped across a heated surface. The outlet temperature is directly related to the heat transferred to the fluid. If fouling occurs, a deposit adheres to the heated surface and insulates a portion of the surface from the test fluid. The insulating deposit reduces the rate of heat transfer to the fluid and its temperature decreases. The rate of change in the fluid temperature is a measure of the rate of fouling.

The time over which temperature measurements are recorded was set at 3 hours. By doing this, the changes in temperatures of several fluids can be used as a measure of their relative fouling tendencies.

The following Examples are reported for illustrative purposes only and are not to be construed as limiting the invention herein described.

Unless specified otherwise, as used herein, all parts and percentages are by weight and based on the total weight of the oil.

EXAMPLES 1-10

Fouling Measurement of Crude Oils by Thermal Fouling Tester

The fouling characteristics (ΔT) of the four crude oils used in this investigation was measured by the thermal fouling tester using the following operation conditions:
Type of heater tube: Two piece C/S tube
Metal temperature (°F): 700
Oil Circulation rate (cc/Min): 3.0
Preheating (°F.): 70
Pressure (psig): 500
Time (hours): 3.0

The fouling characteristics ( T) of four crude oils used in our testing program (Baytown Crudes No. 1 and 2), SJV Crude and Coastal Crude) are given in the Table V below:

TABLE V

| | Fouling Measurement of Untreated Crude No. 1 | | |
| --- | --- | --- | --- |
| Example | Type of Crude Oil | Maximum Fluid Temperature (°F.) | Fouling ΔT (°F.) |
| 1 | Baytown No. 1 | 530 | 66 |
| 2 | Baytown No. 1 | 523 | 62 |
| 3 | Baytown No. 1 | 553 | 51 |
| 4 | Baytown No. 1 | 543 | 53 |
| | | | Average 58 |
| 5 | Baytown No. 2 | 545 | 55 |
| 6 | Baytown No. 2 | 555 | 53 |
| 7 | Baytown No. 2 | 551 | 51 |
| | | | Average 55 |
| 8 | SJV | 550 | 0 |
| 9 | Coastal | 553 | 25 |

EXAMPLES 10-15

HPLC Composition of Four Crude Oils

In the analytical separation, a 3.9 mm by 30 cm long ENERGY ANALYSIS COLUMN commercially available from Waters Associates, 34 Maple Street, Milford, Mass. 01757, U.S.A., was used with n-hexane as the solvent and mobile phase. The samples were "dissolved" in the n-hexane at a volume ratio of 1:40 of sample:solvent. The solution was filtered through a 0.45 micron fluorocarbon membrane filter to remove any insoluble material (asphaltenes).

The "oil " was then injected into the ENERGY ANALYSIS COLUMN. The first peak was the saturates: normal, iso, and cyclosaturates. Any aliphatic unsaturates, eluted at this time. The neutral aromatics, up through six condensed rings, eluted as the next fraction. At this point, the mobile phase was reversed through the column. This was done by the use of a high pressure valve activated by timed events. With the flow in the reverse direction, the polar aromatics eluted. This fraction contained the sulfur, nitrogen and oxygen-containing aromatics. The total instrumental time was 23 minutes.

The neutral aromatics, and polar aromatics were determined from the chromatographic area, times the response factor calculated from the API gravity. When the removal of "asphaltenes" was done quantitatively by filtration, then the saturates were determined by difference.

The analytical separation was done on a dual detector instrument (UV at 254 nm and differential refractometer in series). The column was a 3.9 mm by 30 cm long ENERGY ANALYSIS COLUMN. The solvent and mobile phase was n-hexane.

The flow rate was maintained at 2.0 ml/min at room temperature. The instrument also contained a high pressure valve used in column backflush. The valve was activated from timed events on a M-730 Data Module.

The sample was dissolved in n-hexane at a ratio of 1:40 with 0.5 grams of sample was dissolved in 20 ml of n-hexane. This solution was filtered through a tared 0.45 micron fluorocarbon membrane filter. After the filter was dried, it was re-weighed for the amount of saturates and asphaltenes.

In Table VI below, the results of fractionating various crude oil samples using high performance liquid chromatography according to the above method of the Example, is illustrated:

TABLE VI

| Example | Crude Oil | Saturate Fraction (%) | Neutral Aromatic Fraction (%) | Polar Aromatic Fraction (%) | Asphaltene Fraction (%) | Total Aromatic Fraction (%) |
|---|---|---|---|---|---|---|
| 10 | Coastal | 74.5 | 16.7 | 8.8 | — | 25.8 |
| 11 | Baytown/1 | 86.3 | 10.9 | 2.9 | — | 13.8 |
| 12 | SJV | 55.80 | 21.06 | 21.75 | 1.37 | 42.80 |
| 13 | SJV | 57.02 | 20.76 | 20.87 | 1.37 | 41.60 |
| 14 | Baytown/2 | 87.90 | 6.86 | 2.37 | 3.68 | 9.23 |
| 15 | Baytown/2 | 87.51 | 6.69 | 2.12 | 3.69 | 8.81 |

It will be understood that the present invention is not limited to the above embodiments, but it may be varied and changed without departing from its essence or basic concepts.

What is claimed is:

1. A test method for determining the tendency of a crude oil, including fractions thereof, to foul refinery equipment comprising the steps of removing asphaltenes from a sample of said crude oil; chromatographically separating said sample into a saturated fraction and an aromatic fraction; and measuring at least one of the respective weights of said saturated fraction and said aromatic fraction whereby the tendency of said crude oil to foul said equipment is indicated by the saturated fraction being greater than about 75% of the aromatic fraction being less than about 25 percent.

2. The test method of claim 1 wherein a procedure for separating respective saturated and aromatic fractions includes using a reverse phase high performance liquid chromatography technique.

3. The test method of claim 2 wherein said technique utilizes an Energy Analysis Column.

4. A test method for determining the tendency of particular fractions of crude oil to foul refinery heat-exchanger equipment comprising the steps of fractionating a deasphaltenated sample of said crude oil within a chromatographic column and then measuring the aromatic fraction content, the fouling tendency being indicated by aromatic fraction content of the sample of less than about 25 wt % of the total sample.

5. The test method of claim 4 wherein said fractionating step is accomplished using reverse phase high performance liquid chromatography techniques.

* * * * *